US010966821B2

(12) United States Patent
Delaloye

(10) Patent No.: US 10,966,821 B2
(45) Date of Patent: Apr. 6, 2021

(54) HEART VALVE SEALING SKIRT WITH VARIABLE DIAMETERS

(71) Applicant: Symetis SA, Ecublens (CH)

(72) Inventor: Stephane Delaloye, Buelach (CH)

(73) Assignee: Symetis SA, Ecublens (CH)

( * ) Notice: Subject to any disclaimer, the term of this patent is extended or adjusted under 35 U.S.C. 154(b) by 103 days.

(21) Appl. No.: 16/293,909

(22) Filed: Mar. 6, 2019

(65) Prior Publication Data

US 2019/0274828 A1  Sep. 12, 2019

Related U.S. Application Data

(60) Provisional application No. 62/640,254, filed on Mar. 8, 2018.

(51) Int. Cl.
*A61F 2/24* (2006.01)

(52) U.S. Cl.
CPC .......... *A61F 2/2409* (2013.01); *A61F 2/2418* (2013.01); *A61F 2210/0071* (2013.01); *A61F 2220/0025* (2013.01); *A61F 2240/001* (2013.01)

(58) Field of Classification Search
USPC .................................................. 623/2.1–2.19
See application file for complete search history.

(56) References Cited

U.S. PATENT DOCUMENTS

| | | | |
|---|---|---|---|
| 8,246,678 B2 | 8/2012 | Salahieh et al. | |
| 8,845,720 B2 | 9/2014 | Conklin | |
| 9,089,422 B2 | 7/2015 | Ryan et al. | |
| 9,226,826 B2 | 1/2016 | Rust | |
| 9,492,273 B2 | 11/2016 | Wallace et al. | |
| 9,744,031 B2 | 8/2017 | Girard et al. | |
| 9,814,572 B2 | 11/2017 | Edelman et al. | |
| 9,848,981 B2 | 12/2017 | Suri et al. | |
| 9,895,221 B2 | 2/2018 | Vidlund | |
| 10,028,826 B2 | 7/2018 | Yohanan et al. | |
| 10,098,734 B2 | 10/2018 | Hoang | |
| 2012/0123529 A1* | 5/2012 | Levi ..................... A61F 2/2412 623/2.11 |

(Continued)

FOREIGN PATENT DOCUMENTS

| | | |
|---|---|---|
| WO | 2014140230 | 9/2014 |
| WO | 2015169866 | 11/2015 |
| WO | 2016164209 | 10/2016 |

OTHER PUBLICATIONS

International Search Report and Written Opinion for PCT Application No. PCT/EP2019/055501 dated Jun. 13, 2019 (13 pages).

(Continued)

*Primary Examiner* — Suzette J Gherbi
(74) *Attorney, Agent, or Firm* — Pauly, DeVries Smith & Deffner LLC

(57) ABSTRACT

Embodiments include prosthetic valves and related methods. In an embodiment, an implantable valve is included having a frame that includes a plurality of frame struts. The frame can define a central lumen. An outer skirt can be disposed on an abluminal surface of the frame. The outer skirt can include a flap having a first end and a second end. The first end of the flap can be fixed to the abluminal surface of the frame and the second end can be free to move away from the abluminal surface of the frame. Other embodiments are also included herein.

20 Claims, 14 Drawing Sheets

(56) References Cited

U.S. PATENT DOCUMENTS

| | | | | |
|---|---|---|---|---|
| 2012/0226348 | A1* | 9/2012 | Lane | A61F 2/2418 623/2.4 |
| 2016/0030167 | A1* | 2/2016 | Delaloye | A61F 2/2418 623/2.18 |
| 2016/0324631 | A1* | 11/2016 | Lane | A61F 2/2418 |
| 2017/0000603 | A1* | 1/2017 | Conklin | A61F 2/2409 |
| 2017/0049566 | A1* | 2/2017 | Zeng | A61F 2/2436 |
| 2017/0231761 | A1* | 8/2017 | Cohen-Tzemach | A61F 2/2418 623/2.18 |
| 2017/0348100 | A1 | 12/2017 | Lane et al. | |
| 2018/0318074 | A1 | 11/2018 | Yohanan et al. | |
| 2019/0201193 | A1* | 7/2019 | Delaloye | A61F 2/2412 |
| 2019/0202140 | A1* | 7/2019 | Pelled | B29C 66/53245 |
| 2019/0274832 | A1* | 9/2019 | Delaloye | A61F 2/2463 |
| 2019/0290426 | A1* | 9/2019 | Maimon | A61F 2/958 |
| 2019/0314151 | A1* | 10/2019 | Biadillah | A61F 2/2418 |
| 2019/0321171 | A1* | 10/2019 | Morriss | A61F 2/2418 |
| 2019/0336278 | A1* | 11/2019 | Essinger | A61F 2/2436 |
| 2020/0008938 | A1* | 1/2020 | Yohanan | A61F 2/2436 |
| 2020/0188095 | A1* | 6/2020 | Liu | A61F 2/2412 |

OTHER PUBLICATIONS

Falk, Volkmar "TAVI: Future Developments," Powerpoint presentation from the 4th Aortic Live Symposium Oct. 23-24, 2017 in Hamburg, Germany (74 pages).

Walther, "Acurate neo Aortic Bioprosthesis for Implantation using the Acurate neo TA Transapical Delivery System in Patients with Severe Aortic Stenosis," Clinical Investigation Plan by Symetis S.A., Sep. 8, 2015 retrieved from URL <https://clinicaltrials.gov/ProvidedDocs/28/NCT02950428/Prot_000.pdf> on Mar. 26, 2019 (76 pages).

* cited by examiner heading# HEART VALVE SEALING SKIRT WITH VARIABLE DIAMETERS

This application claims the benefit of U.S. Provisional Application No. 62/640,254, filed Mar. 8, 2018, the content of which is herein incorporated by reference in its entirety.

FIELD OF THE TECHNOLOGY

The present application relates to prosthetic valves and related methods.

BACKGROUND

Heart function can be significantly impaired when a heart valve is not functioning properly. Potential causes for heart valve malfunction include dilation of an annulus around the valve, ventricular dilation, and a prolapsed or misshapen valve leaflet. When the heart valve is unable to close properly, the blood within a heart chamber can regurgitate, or leak backwards through the valve.

Valve regurgitation may be treated by replacing or repairing a diseased valve, such as an aortic valve. Surgical valve replacement is one method for treating the diseased valve. Minimally invasive methods of treatment, such as transcatheter aortic valve replacement (TAVR), generally involve the use of delivery catheters that are delivered through arterial passageways or other anatomical routes into the heart to replace the diseased valve with an implantable prosthetic heart valve. Leaflets of such valves have been formed from various materials including synthetic materials and animal tissues. Valves are normally designed to allow flow in one direction and prevent flow in the opposite direction. Because of systolic and diastolic pressures acting in opposite direction, blood can attempt to flow in both directions. Therefore, valves can be designed with specific attention to preventing blood from flowing counter to the desired direction.

SUMMARY

In a first aspect, an implantable valve is included. The implantable valve can include a frame and an outer skirt. The frame can include a plurality of frame struts. The frame can define a central lumen. The outer skirt can be disposed on an abluminal surface of the frame. The outer skirt can include a flap. The flap can include a first end and a second end. The first end can be fixed to the abluminal surface of the frame and the second end can be free to move away from the abluminal surface of the frame.

In a second aspect, in addition to one or more of the preceding or following aspects, or in the alternative to some aspects, the flap can be an annular flap extending around the frame.

In a third aspect, in addition to one or more of the preceding or following aspects, or in the alternative to some aspects, the implantable valve can further include at least one leaflet disposed within the central lumen.

In a fourth aspect, in addition to one or more of the preceding or following aspects, or in the alternative to some aspects, a portion of the leaflet can have a greater thickness than the flap.

In a fifth aspect, in addition to one or more of the preceding or following aspects, or in the alternative to some aspects, the leaflet can include the same polymer as the outer skirt and the flap.

In a sixth aspect, in addition to one or more of the preceding or following aspects, or in the alternative to some aspects, the inner diameter of the central lumen can be at least 15 mm and not more than 40 mm.

In a seventh aspect, in addition to one or more of the preceding or following aspects, or in the alternative to some aspects, the outer skirt can include a second flap. The second flap can include a first end and a second end. The first end can be adhered to the abluminal surface of the frame and the second end can be free to move away from the abluminal surface of the frame.

In an eighth aspect, in addition to one or more of the preceding or following aspects, or in the alternative to some aspects, the flap and the second flap can be aligned in the same direction such that the first end of the flap and the first end of the second flap can be closer to an inlet of the central lumen and the second end of the flap and the second end of the second flap can be closer to an outlet of the central lumen.

In a ninth aspect, in addition to one or more of the preceding or following aspects, or in the alternative to some aspects, a portion of the outer skirt can be disposed between the abluminal surface of the frame and the flap.

In a tenth aspect, in addition to one or more of the preceding or following aspects, or in the alternative to some aspects, the outer skirt can include a thermoplastic polymer.

In an eleventh aspect, in addition to one or more of the preceding or following aspects, or in the alternative to some aspects, the first end of the flap can be closer to an inlet of the central lumen and the second end of the flap can be closer to an outlet of the central lumen.

In a twelfth aspect, in addition to one or more of the preceding or following aspects, or in the alternative to some aspects, the implantable valve can further include an inner skirt disposed on a luminal surface of the frame.

In a thirteenth aspect, in addition to one or more of the preceding or following aspects, or in the alternative to some aspects, the second end of the flap can be unfixed from the abluminal surface.

In a fourteenth aspect, in addition to one or more of the preceding or following aspects, or in the alternative to some aspects, a method of making an implantable valve is included. The method can include obtaining a frame that define a central lumen. The method can include forming an outer skirt on an abluminal surface of the frame. The method can include positioning a spacer on an outer surface of the outer skirt. The method can include forming a flap. The flap can include a first end and a second end. The first end can be adhered to the abluminal surface of the frame and the second end can be free to move away from the abluminal surface of the frame. The spacer can be disposed between the second end of the flap and the abluminal surface of the frame. The method can also include removing the spacer.

In a fifteenth aspect, in addition to one or more of the preceding or following aspects, or in the alternative to some aspects, the method of making an implantable valve can include forming an inner skirt on a luminal surface of the frame.

In a sixteenth aspect, in addition to one or more of the preceding or following aspects, or in the alternative to some aspects, forming can include molding a thermoplastic polymer.

In a seventeenth aspect, in addition to one or more of the preceding or following aspects, or in the alternative to some aspects, the spacer can be a rectangular strip.

In an eighteenth aspect, in addition to one or more of the preceding or following aspects, or in the alternative to some aspects, the method of making an implantable valve can include positioning a second spacer on the outer portion of the outer skirt. The method can include forming a second flap. The second flap can include a first end and a second end. The first end can be adhered to the abluminal surface of the frame and the second end can be free to move away from the abluminal surface of the frame. The spacer can be disposed between the second end of the flap and the abluminal surface of the frame. The method can further include removing the second spacer.

In a nineteenth aspect, in addition to one or more of the preceding or following aspects, or in the alternative to some aspects, a method of making an implantable valve is included. The method can include obtaining a frame that defines a central lumen. The method can include positioning a spacer on an abluminal surface of the frame. The method can include forming an outer skirt and a flap. The outer skirt can be disposed on the abluminal surface. The flap can include a first end and a second end. The first end can be adhered to the abluminal surface and the second end can be free to move away from the abluminal surface. The spacer can be disposed between the second end of the flap and the abluminal surface. The method can include removing the spacer.

In a twentieth aspect, in addition to one or more of the preceding or following aspects, or in the alternative to some aspects, the method of making an implantable valve of claim can further include positioning a second spacer on the abluminal surface. The method can include forming a second flap that comprises a first end and a second end. The first end can be adhered to the abluminal surface and the second end can be free to move away from the abluminal surface. The second spacer can be disposed between the second end of the flap and the abluminal surface. The method can include removing the second spacer.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present application is defined by the appended claims and their legal equivalents.

BRIEF DESCRIPTION OF THE FIGURES

The technology may be more completely understood in connection with the following drawings, in which.

While the technology is susceptible to various modifications and alternative forms, specifics thereof have been shown by way of example and drawings, and will be described in detail. It should be understood, however, that the application is not limited to the particular embodiments described. On the contrary, the application is to cover modifications, equivalents, and alternatives falling within the spirit and scope of the technology.

DETAILED DESCRIPTION

The human body has four heart valves: a pulmonary valve, a tricuspid valve, an aortic valve and a mitral valve. The purpose of the heart valves is to allow blood to flow in a particular direction through the heart and from the heart into the major blood vessels connected to the heart, such as the aorta and pulmonary artery. Prosthetic valves designed to replace a valve in a human body frequently include two or more leaflets (commonly three) that are attached to a frame. Prosthetic valves can be configured to allow one way flow through the valve, such as by separating the leaflets from each other to open the valve or joining together (valve leaflet coaptation) to close the valve.

In many scenarios the prosthetic valves are configured to allow flow through the valve in one direction, such as under systolic pressure, and prevent flow in the opposite direction, such as under diastolic pressure. The performance of a valve can highly depend on the fit of the valve within a vessel. Various embodiments of a variable diameter sealing skirt and related methods are disclosed herein.

In some embodiments, a sealing skirt or flap can be at least partially fixed to an abluminal surface of a valve frame. The sealing skirt can have a variable diameter in order to conform to the size difference between the valve and the vessel in which it is located. The variable diameter can also allow the valve to conform to the shape of the vessel. The skirt can be configured to prevent flow in an undesired direction, such as flow under diastolic pressure. Under diastolic pressure the flow of blood can reverse direction compared to the flow under systolic pressure. The sealing skirt can include a flap that has a free edge that can separate from the abluminal surface of the valve frame to define a cavity or pocket. The cavity or pocket can block fluid attempting to flow in the unintended direction. The flap can provide a seal between the abluminal surface of the frame and the surrounding vessel thereby preventing backflow.

Figure 1:
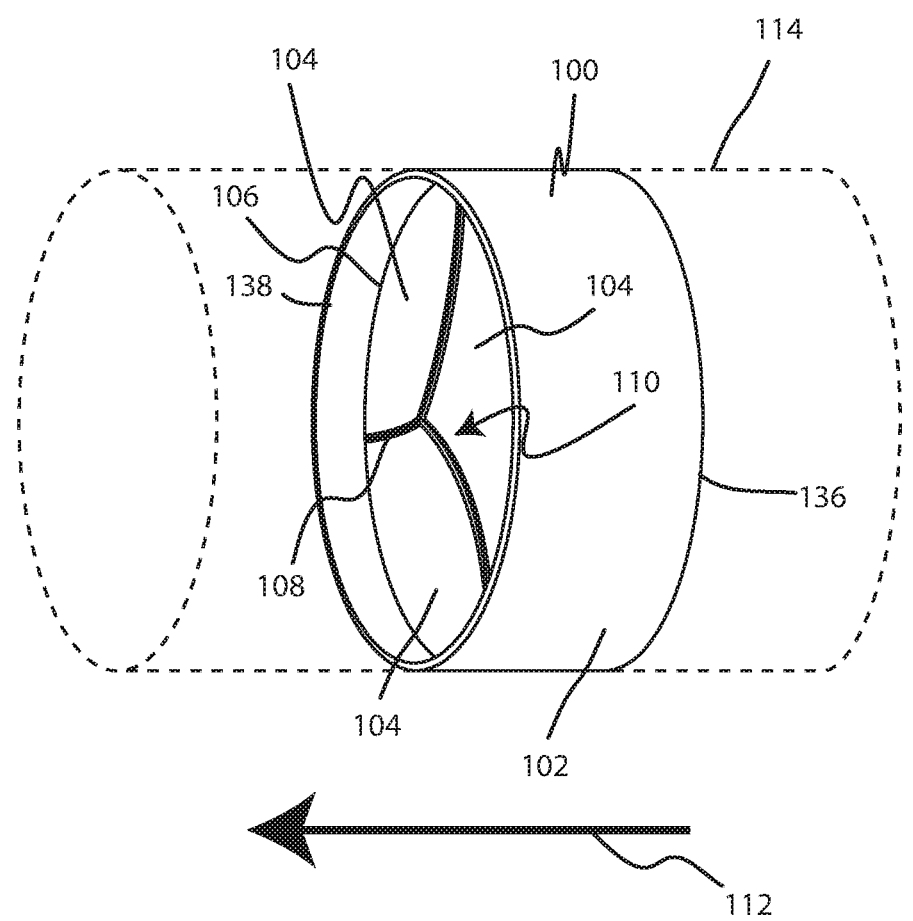
FIG. 1 is a schematic perspective view of a closed valve in a portion of an environment where it can be used, according to various embodiments.
Figure 2:
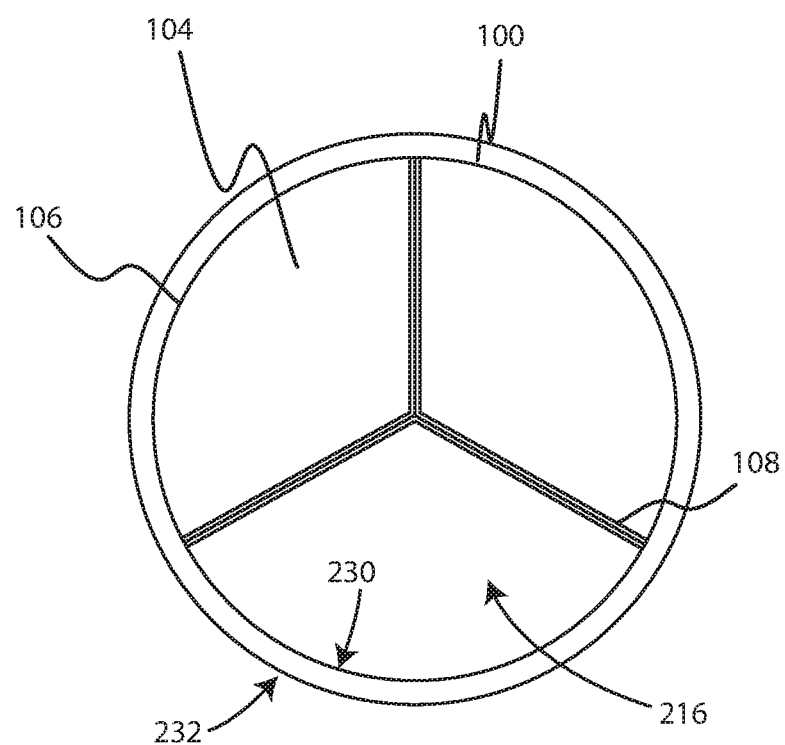
FIG. 2 is a schematic end view of a closed valve in a portion of an environment where it can be used, according to various embodiments.

FIG. 1 shows a schematic view of a closed valve 100 in a vessel 114, according to various embodiments. FIG. 2 shows an end view of the closed valve 100. It should be appreciated that the valve 100 can be any type of heart valve (e.g., a mitral valve, an aortic valve, etc.). In use, the valve 100 can be implanted (e.g., surgically or through transcatheter delivery) in a mammalian heart.

The valve 100 can be configured to allow one-way flow through the valve 100, such as depicted by arrow 112. In an embodiment, the arrow 112 represents blood flow during systolic pressure, such as when the valve 100 is an aortic valve. In other embodiments, the arrow represents blood flow during diastolic pressure, such as when the valve 100 is a mitral valve. Flow opposite to the arrow 112 between the abluminal surface of the frame 102 and the vessel 114 can be prevented by various embodiments disclosed herein. The valve 100 can include an inlet 136 and an outlet 138. The inlet 136 can refer to the upstream portion of the valve 100 where blood enters the valve 100 during flow caused by systolic pressure. The outlet 138 can be the downstream portion of the valve 100 where blood exits the valve 100 during flow caused by systolic pressure.

The valve 100 can include a frame 102 defining a central lumen 216 (see FIG. 2) which, in some embodiments, can be substantially cylindrical. The side of the frame 102 and other components facing the central lumen 216 can be referred to as the luminal surface 230 or luminal side. The opposite side of the frame 102 and other components (e.g., facing away from the central lumen 216) can be referred to as the abluminal surface 232 or abluminal side. In various embodiments, the frame 102 can have a substantially circular cross-section. In other embodiments, the frame 102 can have a non-circular, such as a D-shaped, cross-section. In some embodiments, a non-circular frame 102 can be used to repair a mitral valve or another non-circular valve in the body. The frame 102, including at least some components thereof, can be formed of various materials including, but not limited to, metals and metal alloys, such as corrosion resistant metals and metal alloys, composites, ceramics, polymers, and the like. In some embodiments, the frame 102 can be at least partially formed of nitinol.

The valve 100 can include a plurality of leaflets 104 disposed within the central lumen 216. Each leaflet 104 can include a respective root edge 106 coupled to the frame 102 and a respective free edge or coaptation edge 108 movable relative to the root edge 106 to coapt with the coaptation edges 108 of the other polymeric leaflets 104 along the coaptation region 110. In some embodiments, the plurality of leaflets 104 can be integrally formed with each other, such that the leaflets 104 are formed as a single unit. In some embodiments, a "root edge" can be a formed edge, such as when the leaflets 104 are formed on the frame 102. However, in other embodiments, the valve leaflets 104 can be formed integrally with other structures such as an integral skirt, base structures, liners, leaflets or the like and thus in those circumstances the "root edge" is not actually a cut or otherwise divided edge, but rather is the place opposite the coaptation edge where the valve leaflet integrally meets those other structures.

The coaptation edges 108 of the leaflets 104 move into coaptation with one another in a closed position (FIGS. 1 and 2) to substantially restrict fluid from flowing past the valve 100 in a closed position. The leaflets 104 can coapt to fill up or close the central lumen 216 of the valve 100 thereby impeding the flow of fluid opposite to arrow 112.

Figure 3:
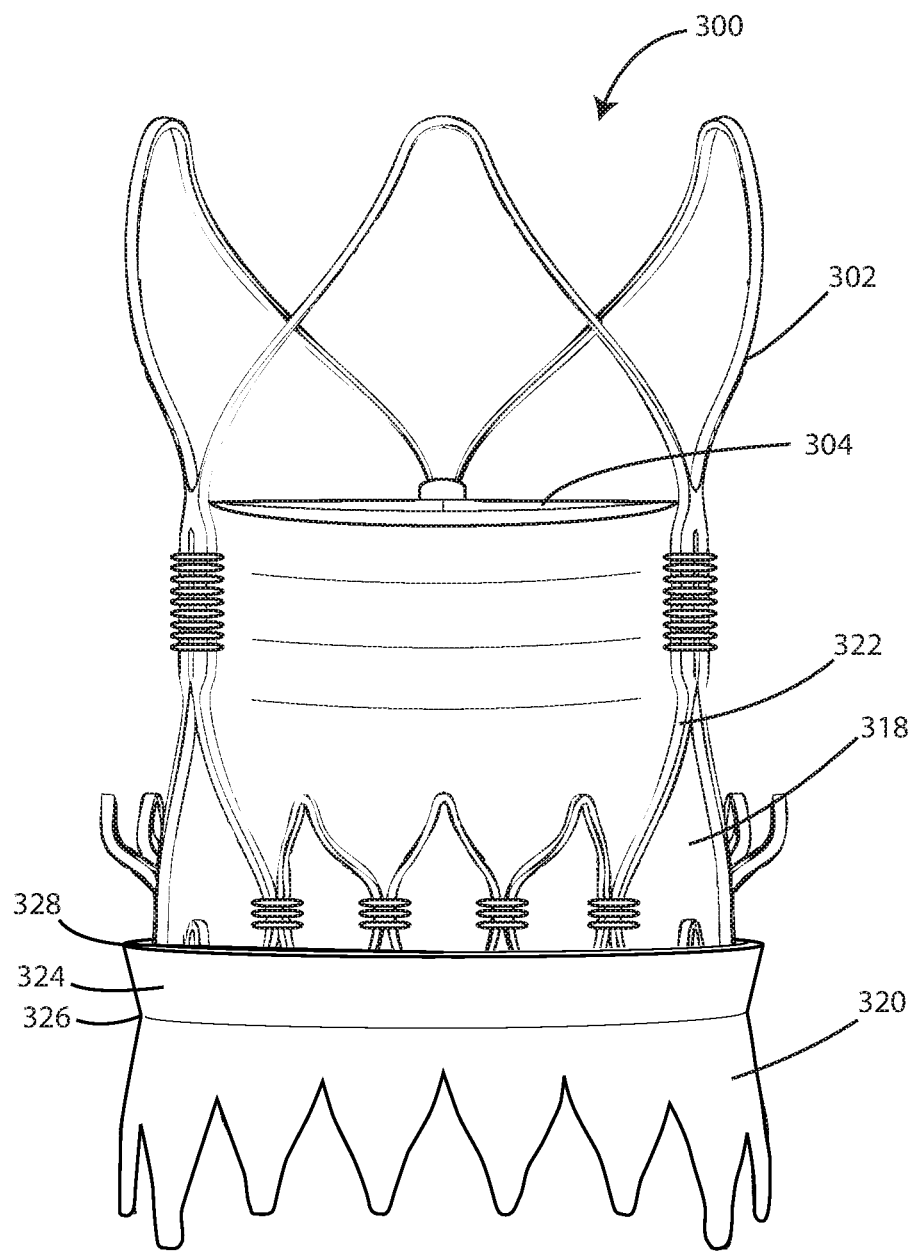
FIG. 3 is a schematic view of an implantable valve, according to various embodiments.

FIG. 3 shows a view of an implantable valve 300, according to various embodiments. The valve 300 can include one or more of: a frame 302, one or more leaflets 304, an inner skirt 318, and an outer skirt 320. The frame 302 can include a plurality of frame struts 322. The frame 302 can define a central lumen 216. The valve leaflets 304 can include a coaptation edge. The valve leaflets 304 can be coupled to the frame 302.

In various embodiments, the implantable valve 300 can include an inner skirt 318. The inner skirt 318 can be disposed on a luminal surface 230 of the frame 302. The luminal surface 230 of the frame 302 can be a surface of the frame 302 that defines the central lumen 216. The inner skirt 318 can direct blood flowing through the valve 300. The inner skirt 318 can ensure the blood flows through the central lumen 216 of the valve 300 and does not flow around the leaflets 304 in a closed configuration during diastolic pressure, such as when the valve is configured as an aortic valve.

In various embodiments, the implantable valve 300 can include an outer skirt 320. The outer skirt 320 can be disposed on an abluminal surface 232 of the frame 302. The abluminal surface 232 of the frame 302 can be a surface of the frame 302 that is external to the central lumen 216. The outer skirt 320 can be disposed between the frame 302 and the vessel wall when the valve is implanted, such as shown in FIGS. 1 and 2, in order to prevent blood from flowing around the valve 300. The outer skirt 320 can ensure the blood flows through the valve 300 and does not flow around the valve 300, such as to ensure the leaflets 304 in a closed position can stop the flow of blood during diastolic pressure.

In various embodiments, the outer skirt 320 can include a flap 324. The flap 324 can include a first end 326 and a second end 328. The first end 326 can be directly or indirectly fixed, attached, or coupled to the abluminal surface 232 of the frame 302. The second end 328 can be free to move away from the abluminal surface 232 of the frame 302. In some embodiments, the second end 328 is unattached or unfixed from the abluminal surface 232 such that the second end 328 can move freely away from or towards the abluminal surface 232. In some embodiments, the flap 324 can be an annular flap, such that the flap 324 extends around the frame 302. In some embodiments, the second end 328 can be attached to the abluminal surface 232 of the frame 302 at one or more discrete locations circumferentially around the frame 302 such that portions of the second end 328 remain free to move away from the abluminal surface 232 while other portions are attached thereto forming pockets.

In some embodiments, the leaflet 304 can be formed of a material that includes a thermoplastic polymer. In some embodiments, the inner skirt 318 can be formed of a material that includes a thermoplastic polymer. In some embodiments, the outer skirt 320 and/or the flap 324 can be formed of a material that includes a thermoplastic polymer. In some embodiments one or more of the leaflet 304, the inner skirt 318, the outer skirt 320 and the flap 324 can be formed of the same material including the same thermoplastic polymer. In some embodiments, the thermoplastic polymer can include polyurethane. In some embodiments one or more of the leaflet 304, the inner skirt 318, the outer skirt 320 and/or the flap 324 can be formed of a biological material, such as bovine pericardium, equine pericardium, or porcine pericardium.

The second end 328 of the flap 324 can flex away from the abluminal surface 232 to form a pocket or cavity 434. The cavity 434 can be configured to catch or block blood flowing in an unintended direction, such as flow during diastolic pressure. The cavity 434 can be seen in the schematic cross-sectional view shown in FIG. 4 (it will be appreciated that FIG. 4 as well as some other figures herein are presented schematically with certain aspects simplified for ease of illustration and clarity). The opening of the cavity can face toward the outlet end of the valve. In some embodiments, the first end 326 of the flap 324 can be disposed closer to the inlet 436 of the valve 300 than the second end 328 of the flap 324. Similarly, the second end 328 of the flap 324 can be disposed closer to the outlet 438 than the first end 326 of the flap 324.

Figure 4:
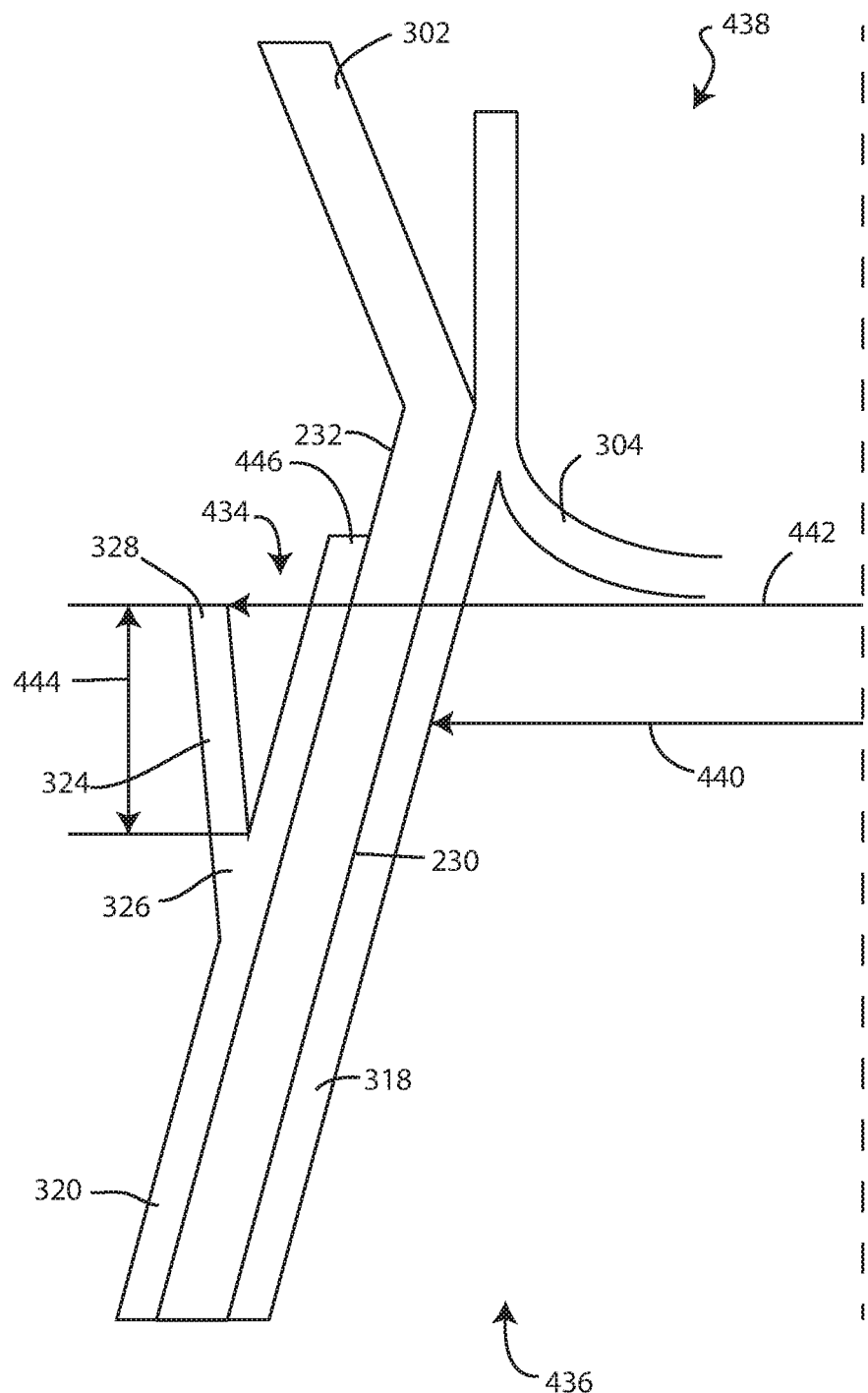
FIG. 4 is a schematic cross-sectional view of a portion of an implantable valve, according to various embodiments.
Figure 12:
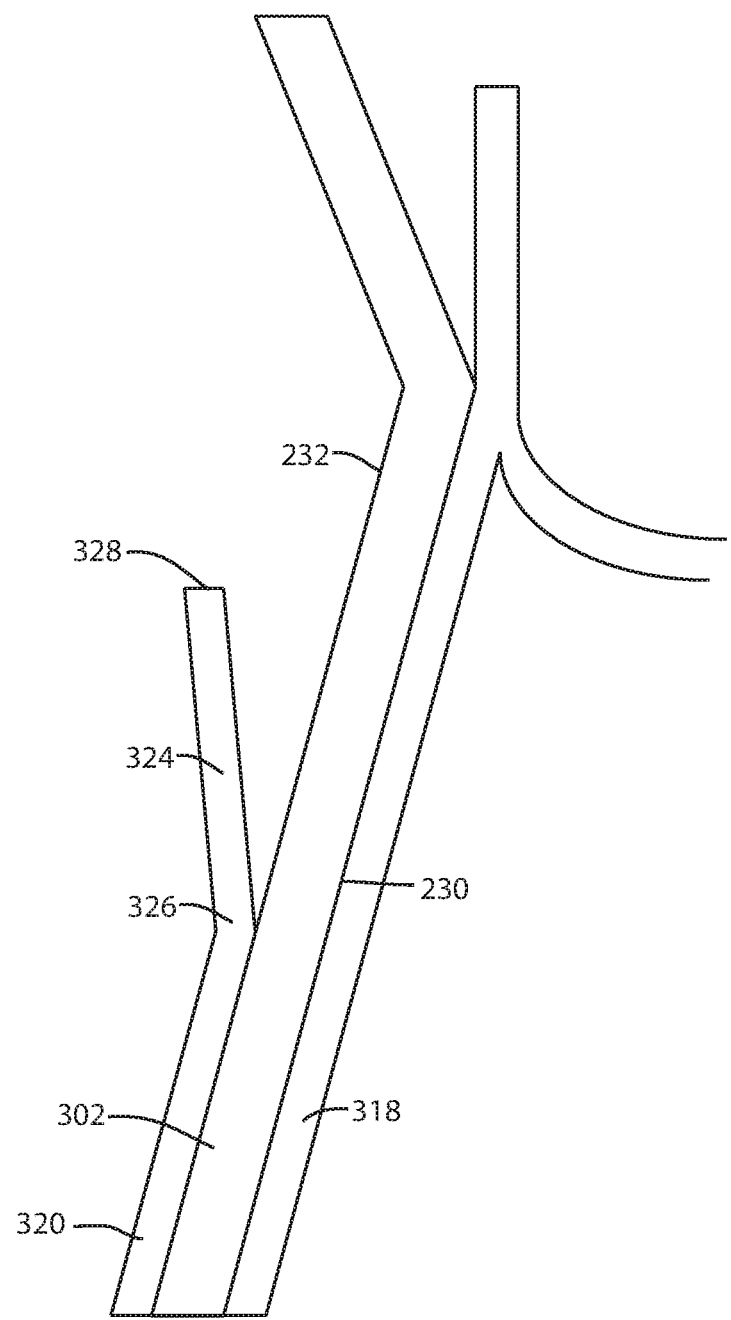
FIG. 12 is a schematic cross-sectional view of a portion of an implantable valve, according to various embodiments.
Figure 13:
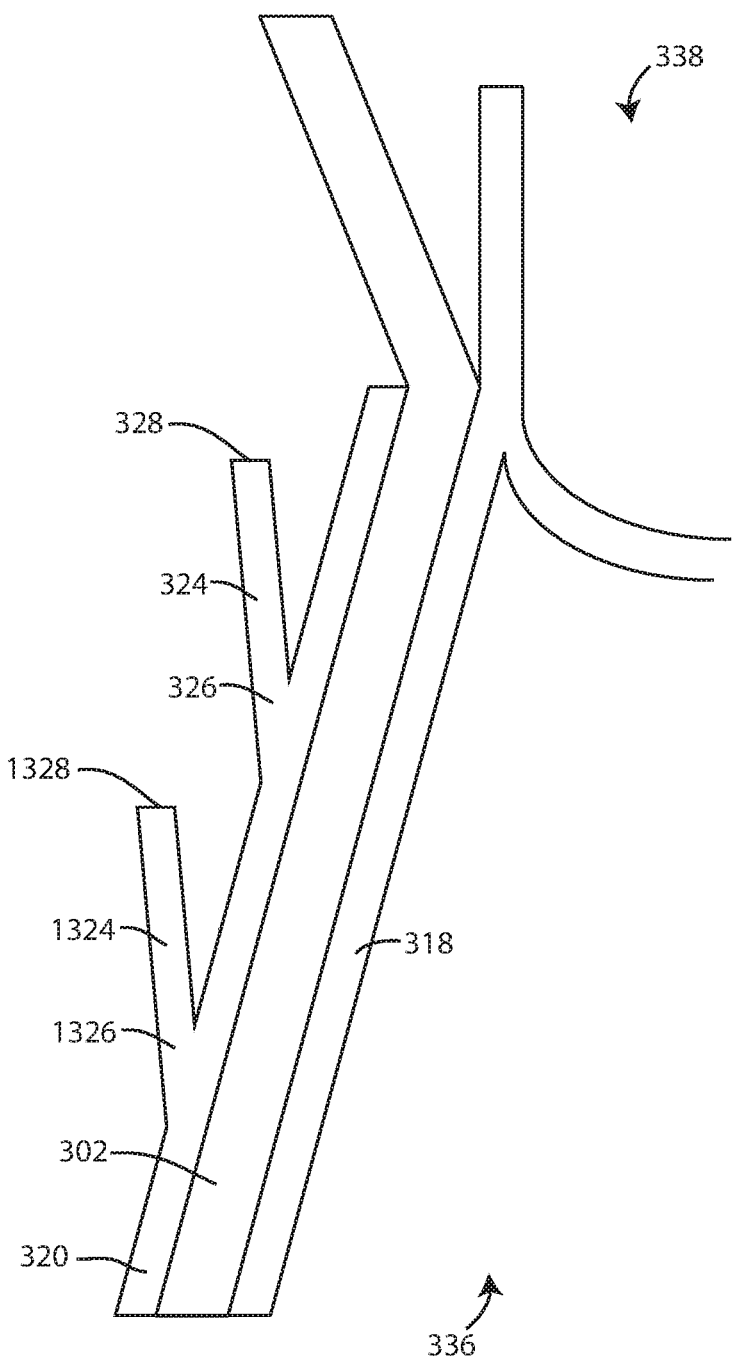
FIG. 13 is a schematic cross-sectional view of a portion of an implantable valve, according to various embodiments.

In some embodiments, a portion 446 of the outer skirt 320 can be disposed between the abluminal surface 232 and the flap 324, such as shown in FIG. 4. In other embodiments, no portion of the outer skirt 320 is disposed between the abluminal surface 232 and the flap 324, such as shown in FIG. 12.

In some embodiments, at least a portion of the leaflet 304 has a thickness that is greater than the thickness of the flap 324. In some embodiments, the thickness of the leaflet 304 is greater than or equal to the thickness of the flap 324.

In various embodiments, the inner diameter 440 of the central lumen 216 can be at least 10 mm and not more than 50 mm. In various embodiments, the inner diameter 440 of the central lumen 216 can be at least 15 mm and not more than 40 mm. In various embodiments, the inner diameter 440 of the central lumen 216 can be at least 20 mm and not more than 35 mm.

In some embodiments, the inner diameter of the flap 442, such as the inner portion of the flap 324 or the diameter of the cavity 434, can be at least 105% of the size of the inner diameter 440 and not more than 130% of the size of the inner diameter 440. In some embodiments, the outer diameter of the flap 324 can be at least 110% of the size of the inner diameter 440 and not more than 125% of the size of the inner diameter 440. In some embodiments, the outer diameter of the flap 324 can be at least 110% of the size of the inner diameter 440 and not more than 120% of the size of the inner diameter 440.

In some embodiments, the flap 324 can have a height 444 of at least 5% of the size of the inner diameter 440 and not more than 50% of the size of the inner diameter 440. In some embodiments, the flap 324 can have a height 444 of at least 10% of the size of the inner diameter 440 and not more than 40% of the size of the inner diameter 440. In some embodiments, the flap 324 can have a height 444 of at least 10% of the size of the inner diameter 440 and not more than 30% of the size of the inner diameter 440.

Figure 5:
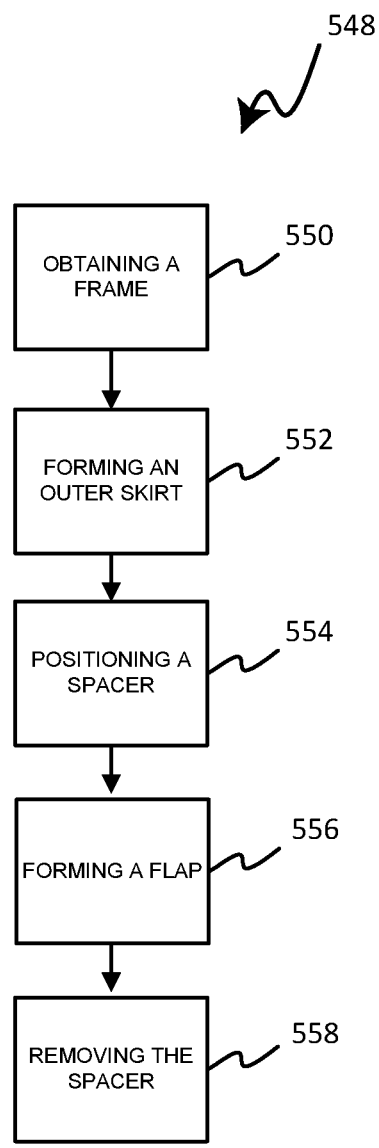
FIG. 5 is a flow chart depicting a method of making an implantable valve, according to various embodiments.

FIG. 5 shows a flow chart depicting a method 548 of making an implantable valve, according to an embodiment. The method 548 can include obtaining a frame 550. As discussed above, the frame 302 can define a central lumen 216.

Figure 6:
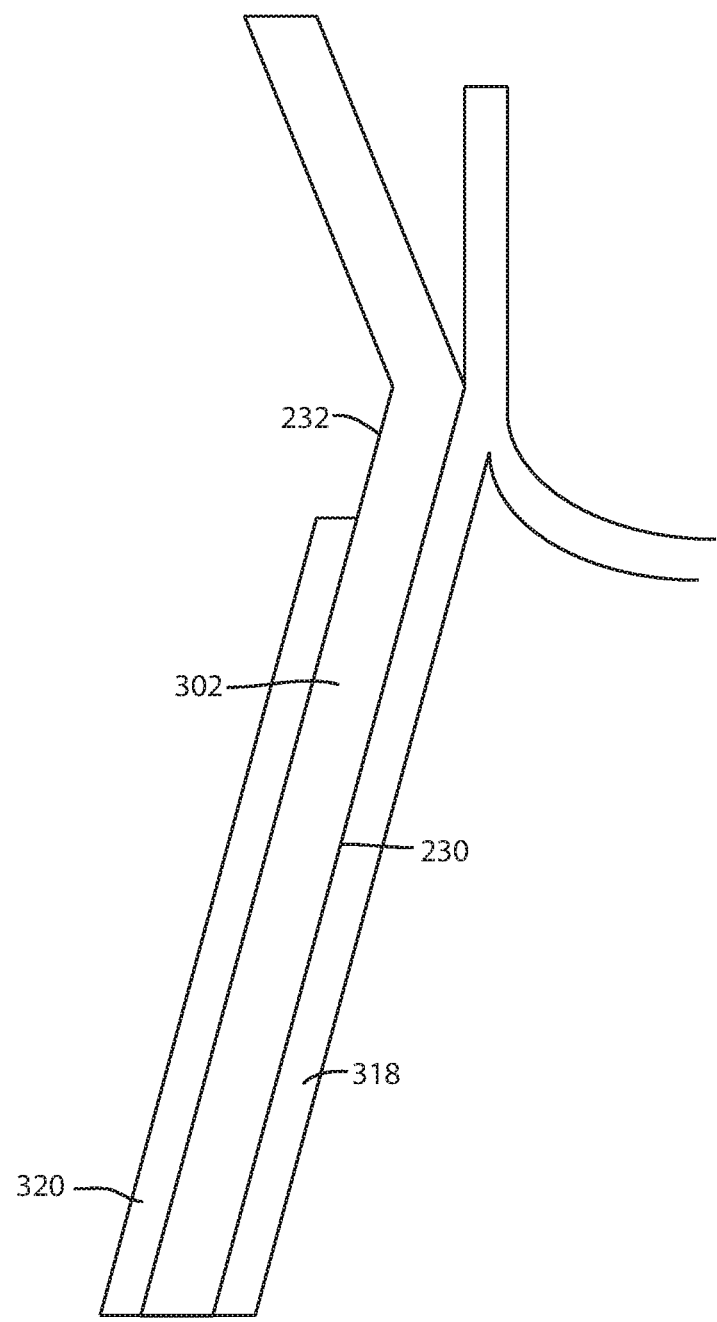
FIG. 6 is a schematic cross-sectional view of a portion of an implantable valve, according to various embodiments.

The method 548 can include forming an outer skirt on the frame 552. The outer skirt can be formed on an abluminal surface of the frame, such as shown in FIG. 6. The method can also include forming an inner skirt on a luminal surface of the frame. In some embodiments, forming can include depositing, molding or otherwise placing a polymer into position. FIG. 6 shows a cross-section of a frame 302 with an outer skirt 320 disposed on the abluminal surface 232 and an inner skirt 318 disposed on a luminal surface 230 of the frame 302, resulting from forming an outer skirt on the frame 552 before, after or simultaneously with forming an inner skirt 318 on the frame 552.

Figure 7:
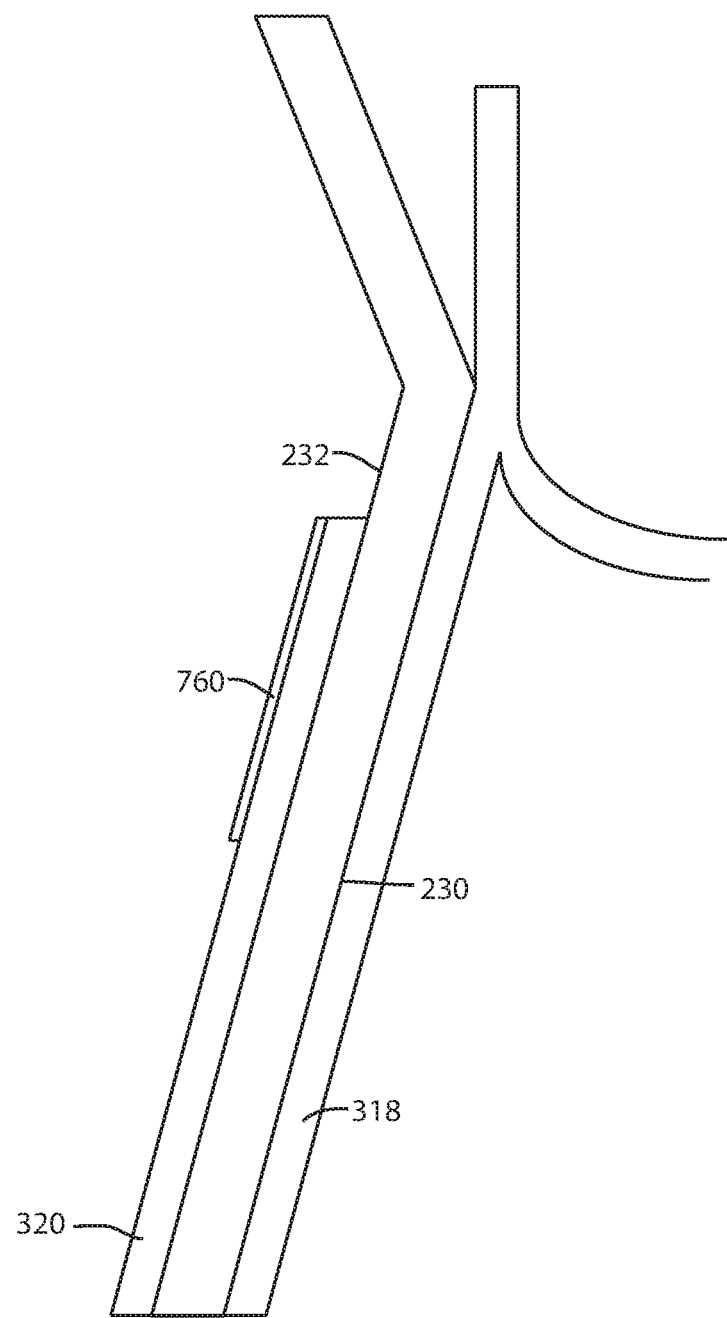
FIG. 7 is a schematic cross-sectional view of a portion of an implantable valve, according to various embodiments.

In some embodiments, the method 548 can further include positioning a spacer 554, such as positioning the spacer on the outer skirt 320. An embodiment of a cross-section of a spacer 760 disposed on the outer skirt 320 is shown in FIG. 7. The spacer 760 can be temporarily disposed on the outer skirt 320, such as only during the forming of a flap or during the manufacturing process. The spacer can be configured to define a gap or separation between the flap and the abluminal surface 232 or a portion of the outer skirt 320.

Figure 8:
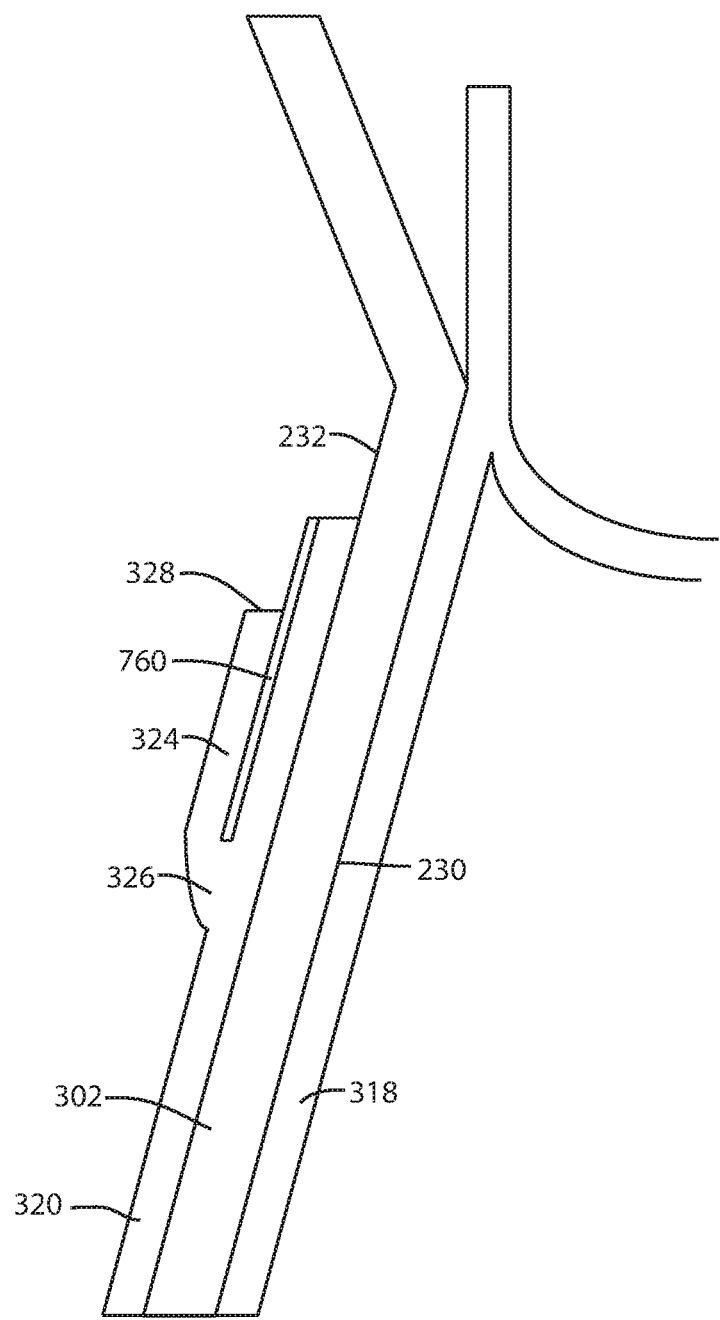
FIG. 8 is a schematic cross-sectional view of a portion of an implantable valve, according to various embodiments.

In various embodiments, the method 548 can also include forming a flap 556. The flap can include a first end and a second end. The first end can be adhered to the abluminal surface of the frame and the second end can be free to move away from the abluminal surface. The spacer 760 can be disposed between the second end 328 of the flap 324 and the abluminal surface 232, as shown in FIG. 8. FIG. 8 shows a cross-section of a frame 302 with the spacer 760 disposed between the flap 324 and a portion of the outer skirt 320. In some embodiments, forming a flap 556 can include depositing or molding a thermoplastic polymer. In some embodiments, the flap 556 can be integrally molded along with the outer skirt 320 or portions thereof.

In various embodiments, the method 548 can also include removing the spacer 760. In some embodiments, the spacer 760 can be formed of a material that does not adhere to or is easily separated from the polymeric material used to form the flap. In some embodiments, the spacer 760 can be formed of PTFE polytetrafluoroethylene), a polysiloxane, polyethylene, or polypropylene. Removing the spacer 760 can define a cavity or separation between the flap 324 and the abluminal surface 232 of the frame 302, such as shown in FIG. 4.

In some embodiments, the method 548 can further include positioning a second spacer, such as on the outer skirt. The method 962 can include forming a second flap that comprises a first end and a second end. The first end can be adhered to the abluminal surface or outer skirt, and the second end can be free to move away from the abluminal surface. The second spacer can be disposed between the second end of the flap and the outer skirt. The method 548 can also include removing the second spacer.

Figure 9:
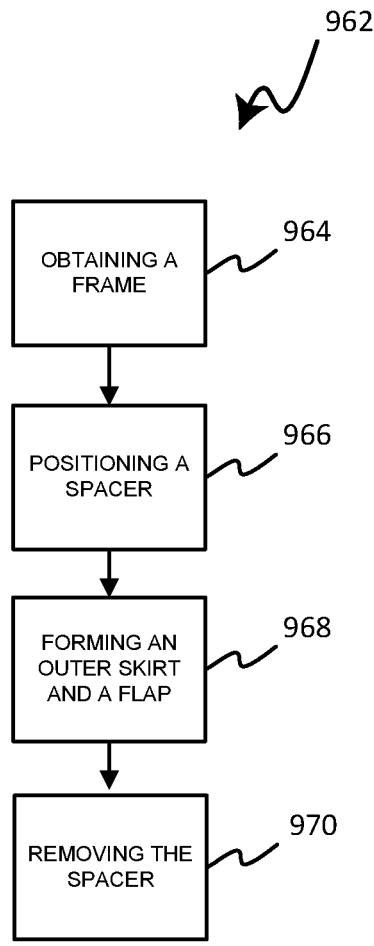
FIG. 9 is a flow chart depicting a method of making an implantable valve, according to various embodiments.

FIG. 9 shows a flow chart depicting a method 962 of making an implantable valve, according to various embodiments. The method 962 can include obtaining a frame 964. As discussed above, the frame 302 can define a central lumen 216.

Figure 10:
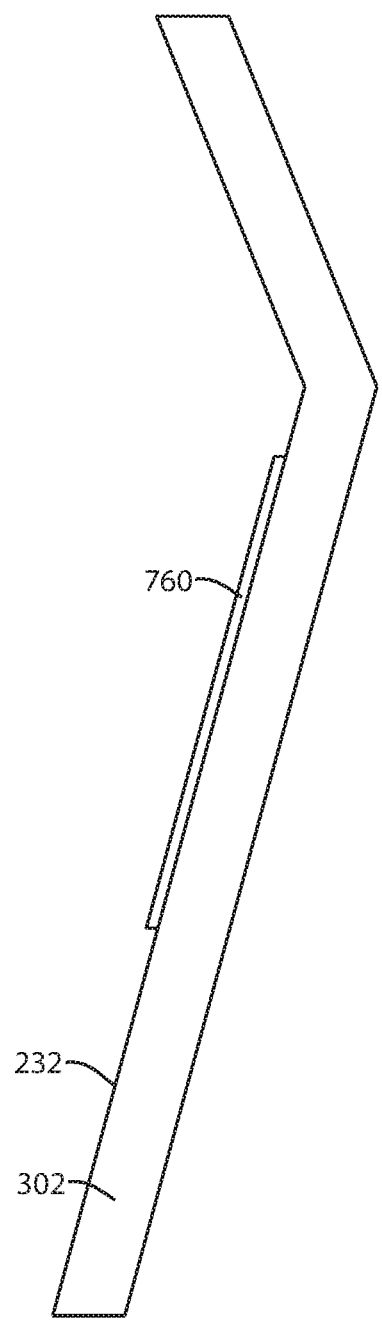
FIG. 10 is a schematic cross-sectional view of a portion of an implantable valve, according to various embodiments.

In some embodiments, the method 962 can further include positioning a spacer 966, such as positioning the spacer 760 on the abluminal surface 232 of the frame 302. An embodiment of a cross-section of a spacer 760 disposed on the abluminal surface 232 of the frame 302 is shown in FIG. 10. The spacer 760 can be temporarily disposed on the abluminal surface 232, such as only during the forming of a flap or during the manufacturing process. The spacer 760 can be configured to define a gap or separation between the flap and the abluminal surface 232.

Figure 11:
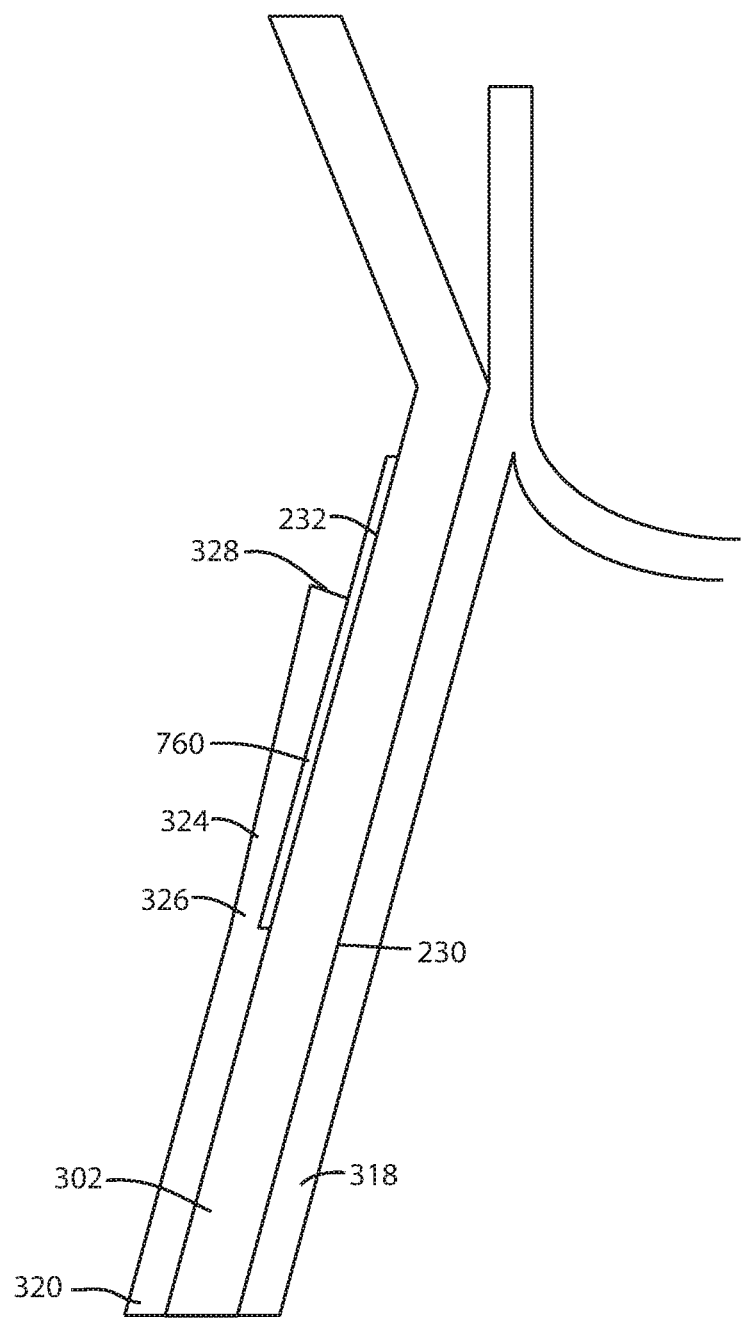
FIG. 11 is a schematic cross-sectional view of a portion of an implantable valve, according to various embodiments.

In various embodiments, the method 962 can include forming an outer skirt and a flap 968. The outer skirt can be formed on an abluminal surface of the frame, such as shown in FIG. 11. The method can also include forming an inner skirt on a luminal surface of the frame. In some embodiments, forming can include depositing or molding a thermoplastic polymer. FIG. 11 shows a cross-section of a frame 302 with an outer skirt 320 disposed on the abluminal surface 232 and a flap 324 disposed on the spacer 760. FIG. 11 further shows an inner skirt 318 disposed on a luminal surface 230 of the frame 302.

As discussed above, the flap can include a first end and a second end. The first end can be adhered to the abluminal surface of the frame and the second end can be free to move away from the abluminal surface. The spacer 760 can be disposed between the second end 328 of the flap 324 and the abluminal surface 232. In some embodiments, forming an outer skirt and a flap 968 can include depositing or molding a thermoplastic polymer.

In various embodiments, the method 962 can also include removing the spacer 970. Removing the spacer 970 can define a cavity between the flap 324 and the abluminal surface 232 of the frame 302, such as shown in FIG. 12.

In some embodiments, the method 962 can further include positioning a second spacer on the abluminal surface. The method 962 can include forming a second flap that comprises a first end and a second end. The first end can be adhered to the abluminal surface and the second end can be free to move away from the abluminal surface. The second spacer can be disposed between the second end of the flap and the abluminal surface. The method 962 can also include removing the second spacer.

In some embodiments, the outer skirt 320 can include a second flap 1324. FIG. 11 shows a cross-sectional view of a portion of an implantable valve 300 with a second flap 1324, according to various embodiments. The second flap 1324 can include a first end 1326 and a second end 1328. Similar to the flap 324, the first end 1326 can be adhered or fixed to the abluminal surface 232 of the frame 302, and the second end 1328 can be free to move away from the abluminal surface 232 of the frame 302.

The flap 324 and the second flap 1324 can be aligned in the same direction, such that the first end 326 of the flap 324 and the first end 1326 of the second flap 1324 are closer to an inlet 336 of the central lumen 216 and the second end 328 of the flap 324 and the second end 1328 of the second flap 1324 are closer to an outlet 338 of the central lumen 216. It should be understood that all descriptions related to the flap 324 are also applicable to the second flap 1324. Similarly, a second spacer can be used in the methods described in FIGS. 5-12 to define the second flap 1324.

Figure 14:
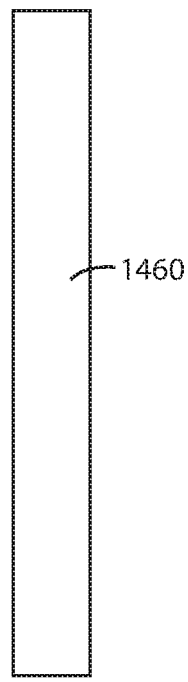
FIG. 14 is a view of a spacer, according to various embodiments.
Figure 15:
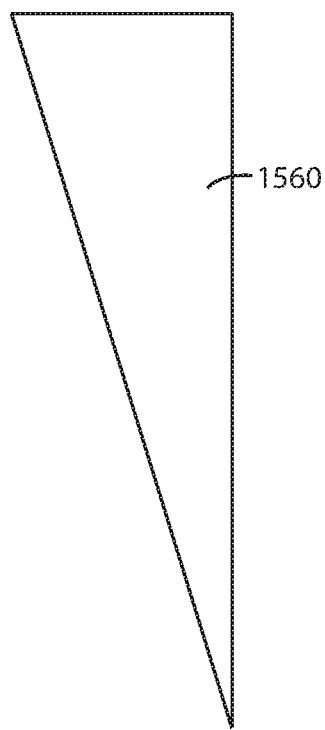
FIG. 15 is a view of a spacer, according to various embodiments.

FIGS. 14 and 15 show spacers according to various embodiments. In some embodiments, the spacer 1460 can be a rectangular strip, such as shown in FIG. 14. The rectangular strip can have a rectangular cross-section. In some embodiments, the spacer 1560 can be a wedge, such as shown in FIG. 15. The wedge can have one end with a larger thickness than the other end, such as to form a cavity or pocket.

Polymers

Many different polymers can be used to form components herein such as the leaflets, inner skirt, outer skirt, flap(s), and the like. In some embodiments, exemplary polymers are synthetic polymers. However, in some embodiments, non-synthetic polymers can also be used. In some embodiments, the polymer can start as a flowable and/or moldable composition. In some embodiments, a state of flowability can be achieved through heating the polymer to a temperature above its melting temperature. After the polymeric composition has been put into position, it can be allowed to cool and/or solidify. In some examples, the polymer can be a thermoplastic polymer. In some embodiments, a state of flowability can be present prior to a possible later step of cross-linking, curing, solvent evaporation and/or polymerization. In some examples, the polymer can be thermoset polymer in a final form.

In some embodiments, polymers herein can include one or more polymers selected from the group consisting of poly(ethylene oxide), polyethylene, polyesters, polyisobutylene polyurethane (PIBU), poly(styrene-block-isobutylene-block-styrene (SIBS), polypropylene, polystyrene, polyvinylchloride, polyisobutylene (PIB), poly(styrene) polyurethanes, polyvinylidene difluoride, poly(methyl methacrylate), polyethylene glycol, polyanilines, polypyrroles, polythiophenes, polyphenols, polyacetylenes, polyphenylenes, polyacrylonitriles, polylactic acids, polycaprolactone, polyglycolides, polyvinyl acetates, polyethylene terephthalate (PET), cellulose acetate, chitosan, proteins, carbohydrates and copolymers including one or more of these. In some embodiments, different portions of the valve can be formed of different polymers or polymer alloys, but in other embodiments the same polymer or polymer alloy can be used.

The embodiments of the present technology described herein are not intended to be exhaustive or to limit the technology to the precise forms disclosed in the following detailed description. Rather, the embodiments are chosen and described so that others skilled in the art can appreciate and understand the principles and practices of the present technology.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this technology pertains. All publications and patent applications are herein incorporated by reference to the same extent as if each individual publication or patent application was specifically and individually indicated by reference.

The technology has been described with reference to various specific and preferred embodiments and techniques. However, it should be understood that many variations and modifications may be made while remaining within the spirit and scope of the technology.

The invention claimed is:

1. An implantable valve, comprising:
   a frame comprising a plurality of frame struts, the frame defines a central lumen; and
   an outer skirt disposed on an abluminal surface of the frame;
   wherein the outer skirt comprises a flap, the flap comprising a first end and a second end, the first end being fixed to the abluminal surface of the frame and the second end being free to move away from the abluminal surface of the frame;
   wherein at least a portion of the outer skirt is disposed between the abluminal surface of the frame and the flap.

2. The implantable valve of claim 1, wherein the flap is an annular flap extending around the frame.

3. The implantable valve of claim 1, further comprising at least one leaflet disposed within the central lumen.

4. The implantable valve of claim 3, wherein the flap has a thickness, and wherein a portion of the leaflet has a greater thickness than the thickness of the flap.

5. The implantable valve of claim 3, wherein the outer skirt comprises a first material, the flap comprises a second material, and the leaflet comprises a third material; and
   wherein the first material, the second material, and the third material, are polymers of the same type.

6. The implantable valve of claim 1, wherein the inner diameter of the central lumen is at least 15 mm and not more than 40 mm.

7. The implantable valve of claim 1, wherein the outer skirt comprises a second flap, the second flap comprising a first end and a second end, the first end being adhered to the abluminal surface of the frame and the second end being free to move away from the abluminal surface of the frame.

8. The implantable valve of claim 7, wherein the flap and the second flap are aligned in the same direction such that the first end of the flap and the first end of the second flap are closer to an inlet of the central lumen and the second end of the flap and the second end of the second flap are closer to an outlet of the central lumen.

9. The implantable valve of claim 1, wherein a portion of the outer skirt is disposed between the abluminal surface of the frame and the flap.

10. The implantable valve of claim 1, wherein the outer skirt is comprised of a thermoplastic polymer.

11. The implantable valve of claim 1, wherein the first end of the flap is closer to an inlet of the central lumen and the second end of the flap is closer to an outlet of the central lumen.

12. The implantable valve of claim 1, further comprising an inner skirt disposed on a luminal surface of the frame.

13. The implantable valve of claim 1, wherein the second end of the flap is unfixed from the abluminal surface.

14. A method of making an implantable valve, comprising:
   obtaining a frame that defines a central lumen;
   forming an outer skirt on an abluminal surface of the frame;
   positioning a spacer on an outer surface of the outer skirt;
   forming a flap that comprises a first end and a second end, the first end being adhered to the abluminal surface of the frame and the second end being free to move away from the abluminal surface of the frame, wherein the spacer is disposed between the second end of the flap and the abluminal surface of the frame; and
   removing the spacer.

15. The method of making an implantable valve of claim 14, further comprising:
   forming an inner skirt on a luminal surface of the frame.

16. The method of making an implantable valve of claim 14, wherein forming comprises molding a thermoplastic polymer.

17. The method of making an implantable valve of claim 14, wherein the spacer is a rectangular strip.

18. The method of making an implantable valve of claim 14, further comprising:
   positioning a second spacer on the outer portion of the outer skirt;
   forming a second flap that comprises a first end and a second end, the first end being adhered to the abluminal surface of the frame and the second end being free to move away from the abluminal surface of the frame, wherein the spacer is disposed between the second end of the flap and the abluminal surface of the frame; and
   removing the second spacer.

19. A method of making an implantable valve, comprising:
   obtaining a frame that defines a central lumen;
   positioning a spacer on an abluminal surface of the frame;
   forming an outer skirt and a flap, wherein the outer skirt is disposed on the abluminal surface and the flap comprises a first end and a second end, the first end being adhered to the abluminal surface and the second end being free to move away from the abluminal surface, wherein the spacer is disposed between the second end of the flap and the abluminal surface; and
   removing the spacer.

20. The method of making an implantable valve of claim 19, further comprising:
   positioning a second spacer on the abluminal surface;
   forming a second flap that comprises a first end and a second end, the first end being adhered to the abluminal surface and the second end being free to move away from the abluminal surface, wherein the second spacer is disposed between the second end of the flap and the abluminal surface; and
   removing the second spacer.

* * * * *